US012616838B2

(12) United States Patent
Penninger et al.

(10) Patent No.: US 12,616,838 B2
(45) Date of Patent: May 5, 2026

(54) PATIENT SPECIFIC FREQUENCY MAPPING PROCEDURE FOR HEARING IMPLANT ELECTRODE ARRAYS

(71) Applicant: MED-EL Elektromedizinische Geräte Ges.m.b.H., Innsbruck (AT)

(72) Inventors: Richard Penninger, Innsbruck (AT); Mathias Kals, Grinzens (AT); Reinhold Schatzer, Axams (AT); Dirk Meister, Innsbruck (AT); Peter Nopp, Axams (AT); Daniel Hofer, Axams (AT)

( * ) Notice: Subject to any disclaimer, the term of this patent is extended or adjusted under 35 U.S.C. 154(b) by 319 days.

(21) Appl. No.: 18/043,652

(22) PCT Filed: Oct. 1, 2021

(86) PCT No.: PCT/EP2021/025380
§ 371 (c)(1),
(2) Date: Mar. 1, 2023

(87) PCT Pub. No.: WO2022/069081
PCT Pub. Date: Apr. 7, 2022

(65) Prior Publication Data
US 2023/0347148 A1        Nov. 2, 2023

(30) Foreign Application Priority Data
Oct. 1, 2020    (EP) ...................................... 20199722

(51) Int. Cl.
*A61N 1/36* (2006.01)

(52) U.S. Cl.
CPC ................................ *A61N 1/36039* (2017.08)

(58) Field of Classification Search
CPC .................................................. A61N 1/36039
See application file for complete search history.

(56) References Cited

U.S. PATENT DOCUMENTS

| | | | |
|---|---|---|---|
| 7,010,354 | B1 | 3/2006 | Grayden et al. |
| 10,357,655 | B2 * | 7/2019 | Okuyama ............ A61N 1/0541 |
| 2008/0215332 | A1 | 9/2008 | Zeng et al. |
| 2013/0245717 | A1 | 9/2013 | Stohl et al. |

OTHER PUBLICATIONS

International Searching Authority/EP; International Search Report and Written Opinion of the International Searching Authority, Application No. PCT/EP2021/025380, dated Jan. 24, 2022, 9 pages.

* cited by examiner

*Primary Examiner* — George R Evanisko
(74) *Attorney, Agent, or Firm* — Barclay Damon LLP

(57) ABSTRACT

A patient-specific frequency mapping procedure, a fitting system for carrying out said procedure and computer program product for a cochlear implant or an electric-acoustic stimulation device having an electrode array that has been implanted into the cochlea of said patient is disclosed.

15 Claims, 5 Drawing Sheets

| Electrode | Lower F. [Hz] | Center F. [Hz] | Upper F. [Hz] |
|---|---|---|---|
| 1 | | 376 | |
| 2 | | 532 | |
| 3 | | 802 | |
| 4 | | 1177 | |
| 5 | | 1589 | |
| 6 | | 2224 | |
| 7 | | 2877 | |
| 8 | | 3710 | |
| 9 | | 4660 | |
| 10 | | 6165 | |
| 11 | | 8450 | |
| 12 | | 11874 | |

Fig. 5

| Electrode | Lower F. [Hz] | Center F. [Hz] | Upper F. [Hz] |
|---|---|---|---|
| 1 | 70 | 259 | 447 |
| 2 | 447 | 550 | 653 |
| 3 | 653 | 812 | 971 |
| 4 | 971 | 1169 | 1367 |
| 5 | 1367 | 1623 | 1879 |
| 6 | 1879 | 2204 | 2529 |
| 7 | 2529 | 2898 | 3267 |
| 8 | 3267 | 3712 | 4157 |
| 9 | 4157 | 4758 | 5359 |
| 10 | 5359 | 6288 | 7217 |
| 11 | 7217 | (8616) | (10016) |
| 12 | (10016) | (?) | 8500 |

Fig. 6

| Electrode | Lower F. [Hz] | Center F. [Hz] | Upper F. [Hz] |
|---|---|---|---|
| 1 | 70 | 172 | 273 |
| 2 | 273 | 416 | 558 |
| 3 | 558 | 765 | 972 |
| 4 | 972 | 1170 | 1368 |
| 5 | 1368 | 1624 | 1880 |
| 6 | 1880 | 2205 | 2530 |
| 7 | 2530 | 2898 | 3267 |
| 8 | 3267 | 3611 | 3956 |
| 9 | 3956 | 4372 | 4789 |
| 10 | 4789 | 5294 | 5798 |
| 11 | 5798 | 6409 | 7020 |
| 12 | 7020 | 7760 | 8500 |

Comparison logspace vs. 1ˢᵗ/2ⁿᵈ determination rule

| | 1 | 2 | 3 | 4 |
|---|---|---|---|---|
| 2nd determin. rule | 70 | 273 | 558 | 972 |
| logspace | 70 | 168 | 404 | 972 |
| 1st determin. rule | 70 | 447 | 653 | 972 |

PATIENT SPECIFIC FREQUENCY MAPPING PROCEDURE FOR HEARING IMPLANT ELECTRODE ARRAYS

CROSS-REFERENCE TO RELATED APPLICATIONS

This application is a 371 national phase entry of Patent Cooperation Treaty Application PCT/EP2021/025380, filed Oct. 1, 2021, which in turn claims priority from EP 201997228, filed Oct. 1, 2020. Each of the above-described applications is hereby incorporated herein by reference in it entirety.

FIELD OF THE INVENTION

The present invention relates to hearing implant systems, and more specifically, to techniques for patient-specific frequency mapping in a cochlear implant or an electro-acoustic stimulation device having an electrode array.

BACKGROUND ART

A normal ear transmits sounds as shown in FIG. 1 through the outer ear 101 to the tympanic membrane 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the *scala* vestibuli and a lower channel known as the *scala tympani*, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, hearing prostheses have been developed. For example, when the impairment is related to operation of the middle ear 103, a conventional hearing aid may be used to provide mechanical stimulation to the auditory system in the form of amplified sound. Or when the impairment is associated with the cochlea 104, a cochlear implant with an implanted stimulation electrode array 110 can electrically stimulate auditory nerve tissue with small currents delivered by multiple electrode contacts 112 distributed along the electrode array 110.

FIG. 1 also shows some components of a typical cochlear implant system, including an external microphone that provides an audio signal input to an external signal processor 111 where various signal processing schemes can be implemented. The processed signal is then converted into a digital data format, such as a sequence of data frames, for transmission into the implant 108. Besides receiving the processed audio information, the implant 108 also performs additional signal processing such as error correction, pulse formation, etc., and produces a stimulation pattern (based on the extracted audio information) that is sent through an electrode lead 109 to the implanted electrode array 110.

Typically, the electrode array 110 includes multiple electrode contacts 112 on its surface that provide selective stimulation of the cochlea 104. Depending on context, the electrode contacts 112 are also referred to as electrode channels. In cochlear implants today, a relatively small number of electrode channels are each associated with relatively broad frequency bands, with each electrode contact 112 addressing a group of neurons with an electric stimulation pulse having a charge that is derived from the instantaneous amplitude of the signal envelope within that frequency band.

In some coding strategies, stimulation pulses are applied at a constant rate across all electrode channels, whereas in other coding strategies, stimulation pulses are applied at a channel-specific rate. Various specific signal processing schemes can be implemented to produce the electrical stimulation signals. Signal processing approaches that are well-known in the field of cochlear implants include continuous interleaved sampling (CIS), channel specific sampling sequences (CSSS) (as described in U.S. Pat. No. 6,348,070, incorporated herein by reference), spectral peak (SPEAK), and compressed analog (CA) processing.

FIG. 2 shows various functional blocks in a signal processing arrangement for producing electrode stimulation signals to electrode contacts in an implanted cochlear implant array according to a typical hearing implant system. A pseudo code example of such an arrangement can be set forth as:

Input Signal Preprocessing:
    BandPassFilter (input_sound, band_pass_signals)
    Envelope Extraction:
    BandPassEnvelope (band_pass_signals, band_pass_enve-
        lopes)
    Stimulation Timing Generation:
    TimingGenerate (band_pass_signals, stim_timing)
    Pulse Generation:
    PulseGenerate (band_pass_envelopes, stim_timing, out-
        _pulses)

In the arrangement shown in FIG. 2, the initial input sound signal is produced by one or more sensing microphones, which may be omnidirectional and/or directional. Preprocessor Filter Bank 201 pre-processes this input sound signal with a bank of multiple parallel band pass filters (e.g. Infinite Impulse Response (IIR) or Finite Impulse Response (FIR)), each of which is associated with a specific band of audio frequencies, for example, using a filter bank with 12 digital Butterworth band pass filters of 6th order, Infinite Impulse Response (IIR) type, so that the acoustic audio signal is filtered into some K band pass signals, $U_1$ to $U_K$ where each signal corresponds to the band of frequencies for one of the band pass filters. Each output of sufficiently narrow CIS band pass filters for a voiced speech input signal may roughly be regarded as a sinusoid at the center frequency of the band pass filter which is modulated by the envelope signal. This is also due to the quality factor ($Q \approx 3$) of the filters. In case of a voiced speech segment, this envelope is approximately periodic, and the repetition rate is equal to the pitch frequency. Alternatively and without limitation, the Preprocessor Filter Bank 201 may be implemented based on use of a fast Fourier transform (FFT) or a short-time Fourier transform (STFT). Based on the tonotopic organization of the cochlea, each electrode contact in the *scala tympani* typically is associated with a specific band pass filter of the Preprocessor Filter Bank 201. Associating specific frequency bands with individual electrode contacts is referred to as "frequency mapping" herein. The Preprocessor Filter Bank 201 also may perform other initial signal processing functions such as and without limitation automatic gain control (AGC) and/or noise reduction and/or wind noise reduction and/or beamforming and other well-known signal enhancement functions.

FIG. 3 shows an example of a short time period of an input speech signal from a sensing microphone, and FIG. 4 shows the microphone signal decomposed by band-pass filtering by a bank of filters. An example of pseudocode for an infinite impulse response (IIR) filter bank based on a direct form II transposed structure is given by Fontaine et al., *Brian Hears: Online Auditory Processing Using Vectorization Over Channels*, Frontiers in Neuroinformatics, 2011; incorporated herein by reference in its entirety.

The band pass signals $U_1$ to $U_K$ (which can also be thought of as electrode channels) are output to an Envelope Detector 202 and Fine Structure Detector 203. The Envelope Detector 202 extracts characteristic envelope signals outputs $Y_1, \ldots, Y_K$ that represent the channel-specific band pass envelopes. The envelope extraction can be represented by $Y_k = LP(|U_k|)$, where $|.|$ denotes the absolute value and $LP(.)$ is a low-pass filter; for example, using 12 rectifiers and 12 digital Butterworth low pass filters of 2nd order, IIR-type. Alternatively, the Envelope Detector 202 may extract the Hilbert envelope, if the band pass signals $U_1, \ldots, U_K$ are generated by orthogonal filters.

The Fine Structure Detector 203 functions to obtain smooth and robust estimates of the instantaneous frequencies in the signal channels, processing selected temporal fine structure features of the band pass signals $U_1, \ldots, U_K$ to generate stimulation timing signals $X_1, \ldots, X_K$. The band pass signals $U_1, \ldots, U_k$ can be assumed to be real valued signals, so in the specific case of an analytic orthogonal filter bank, the Fine Structure Detector 203 considers only the real valued part of $U_k$. The Fine Structure Detector 203 is formed of K independent, equally-structured parallel sub-modules.

The extracted band-pass signal envelopes $Y_1, \ldots, Y_K$ from the Envelope Detector 202, and the stimulation timing signals $X_1, \ldots, X_K$ from the Fine Structure Detector 203 are input signals to a Pulse Generator 204 that produces the electrode stimulation signals Z for the electrode contacts in the implanted electrode array 205. The Pulse Generator 204 applies a patient-specific mapping function—for example, using instantaneous nonlinear compression of the envelope signal (map law) that is adapted to the needs of the individual cochlear implant user during fitting of the implant in order to achieve natural loudness growth. The Pulse Generator 204 may apply logarithmic function with a form-factor C as a loudness mapping function, which typically is identical across all the band pass analysis channels. In different systems, different specific loudness mapping functions other than a logarithmic function may be used, with just one identical function is applied to all channels or one individual function for each channel to produce the electrode stimulation signals. The electrode stimulation signals typically are a set of symmetrical biphasic current pulses.

In the CIS strategy, the signal processor only uses the band pass signal envelopes for further processing, i.e., they contain the entire stimulation information. For each electrode channel, the signal envelope is represented as a sequence of biphasic pulses at a constant repetition rate. A characteristic feature of CIS is that the stimulation rate is equal for all electrode channels and there is no relation to the center frequencies of the individual channels. It is intended that the pulse repetition rate is not a temporal cue for the patient (i.e., it should be sufficiently high so that the patient does not perceive tones with a frequency equal to the pulse repetition rate). The pulse repetition rate is usually chosen at greater than twice the bandwidth of the envelope signals (based on the Nyquist theorem).

Another cochlear implant stimulation strategy that does transmit fine time structure information is the Fine Structure Processing (FSP) strategy by Med-El. Zero crossings of the band pass filtered time signals are tracked, and at each negative to positive zero crossing, a Channel Specific Sampling Sequence (CSSS) is started. Typically CSSS sequences are only applied on the first one or two most apical electrode channels, covering the frequency range up to 200 or 330 Hz. The FSP arrangement is described further in Hochmair I, Nopp P, Jolly C, Schmidt M, Schößer H, Garnham C, Anderson I, *MED-EL Cochlear Implants: State of the Art and a Glimpse into the Future*, Trends in Amplification, vol. 10, 201-219, 2006, which is incorporated herein by reference.

The default frequency mapping procedures for cochlear implant and electric-acoustic stimulation devices capitalize on the tonotopic organization of the cochlea by distributing low frequency information at the apical end of the electrode array and high-frequency information at the base. For this, conventionally a fixed frequency mapping is utilized independently of the patients' cochlear size and inserted electrode depth, often resulting in discrepancies between the distribution of frequency information and the natural tonotopic organization of the cochlea, known as a frequency-to-place mismatch. This is one factor that can lead to discrepancies in performance and hearing quality amongst CI and EAS users.

Adding further complexity, there are marked interindividual anatomic variations in cochlear size and cochlear duct length. This may be of importance in postlingually deafened CI recipients, who are familiarized with a natural frequency-to-place function before hearing loss and must adapt to varying degrees of mismatch when listening with a CI-alone or EAS device.

There have been attempts to use electrode position information and associated place frequencies for the organ of *Corti* or spiral ganglion for a more natural frequency mapping. For example, it is conceivable to determine frequency bands by calculating arithmetic or geometric means of the place frequencies of neighboring electrodes. It is however seen in practice that the resulting frequency range that depends on the electrode position and can vary extremely from patient to patient and cannot be expected to give viable frequency mappings. In particular, the resulting frequencies are often found to exceed the possibilities of the hardware, such that the corresponding channels/electrodes have to be disabled.

SUMMARY OF THE INVENTION

A problem underlying the invention is to provide frequency mapping techniques that allow for improved hearing performance. This problem is solved by a patient-specific frequency mapping procedure according to claim 1, as well as by a fitting system according to claim 14 and a computer program product according to claim 14. Preferable embodiments are defined in the dependent claims.

Embodiments of the present invention are directed to a patient-specific frequency mapping procedure for a cochlear implant or an electric-acoustic stimulation device having an electrode array that has been implanted into the cochlea of said patient, wherein said implanted electrode array comprises a number of stimulation electrodes at corresponding electrode locations within the cochlea. Herein, a "stimulation electrode" may correspond to an individual electrode contact of the type shown under reference sign 112 in FIG. 1. However, the expression "stimulation electrode" could merely refer to members of a subset of activated electrode contacts. Namely, in practical applications, it may occur that not all of the available electrode contacts can actually be used, such that one or more of the available physical stimulation contacts may have to be deactivated. In such a scenario, the term "stimulation electrode" may refer to electrode contacts that are not deactivated. Finally, the term "stimulation electrode" may also refer to a so-called "virtual electrode contact", which is formed by cooperative operation of two or more physical electrode contacts, such as two adjacent electrode contacts that are stimulated simultaneously or in rapid succession, thereby producing a stimulation electrical field or current that has its maximum amplitude at a location that is different from the locations of the individual electrode contacts, but for example at a location between the individual electrode contacts, where a "virtual electrode contact" is thereby formed. Indeed, such a virtual electrode contact does not necessarily have to be located between the two underlying physical electrode contacts, but could in some cases be formed outside this interval as well e.g. using partial bipolar stimulation. Accordingly, wherever reference is made to a "stimulation electrode" in the following, this may also refer to "virtual electrode contacts".

The procedure further comprises providing or receiving tonotopic frequency information, said tonotopic frequency information comprising, for each of said stimulation electrodes, a place frequency associated with the patient-specific location of said stimulation electrode in the cochlea where said stimulation electrode is placed.

The procedure further comprises a step of determining, based on said tonotopic frequency information and a tonotopic subset selection criterion, a tonotopic subset of adjacent stimulation electrodes. The procedure further comprises assigning a tonotopic frequency band to each stimulation electrode within said tonotopic subset based on a first band boundary determination rule, wherein said first band boundary determination rule determines an upper and a lower boundary of the tonotopic frequency band for each given stimulation electrode within said tonotopic subset, such as to ensure that the lower boundary is at a frequency that is lower than the place frequency of the given stimulation electrode but higher than the place frequency of the adjacent electrode in apical direction, and the upper boundary is at a frequency that is higher than the place frequency of the given stimulation electrode but lower than the place frequency of the adjacent electrode in basal direction, wherein said tonotopic frequency bands associated with said tonotopic subset of stimulation electrodes define a tonotopic frequency range. Herein, the first band boundary determination rule may determine the upper and lower limits based at least in part on the place frequencies of stimulation electrodes adjacent to said given stimulation electrode in apical and basal direction.

The procedure further comprises a step of assigning a lower boundary to a frequency band associated with the most apical stimulation electrode within the electrode array, said lower boundary being lower than 200 Hz, preferably lower than 150 Hz, and most preferably between 20 and 120 Hz irrespectively of the place frequency of the most apical stimulation electrode.

The procedure further comprises a step of assigning an upper boundary to a frequency band associated with the most basal stimulation electrode, said upper boundary being lower than 20 kHz, preferably lower than 10.0 kHz, and most preferably between 7.5 kHz and 9.5 kHz, irrespectively of the place frequency of the most basal stimulation electrode.

Moreover, the procedure further comprises a step of determining an apical frequency band for each stimulation electrode in an apical subset of stimulation electrodes based on a second band boundary determination rule, said apical frequency bands covering an apical frequency range extending between the tonotopic frequency range and said lower boundary of said frequency band associated with the most apical stimulation electrode. Herein, the "apical subset" comprises all stimulation electrodes to the apical side of said tonotopic subset of stimulation electrodes.

Herein, the second band boundary determination rule is in some embodiments independent of the place frequencies of the stimulation electrodes in said apical subset.

However, the invention is not limited to this, and in other embodiments it is possible that the second band boundary determination rule does account for some or all of said place frequencies associated with said apical subset. However, in this case, the second band boundary determination rule is still different from the first band boundary determination rule, and in particular leads to a distribution of boundaries that is closer to a logarithmically evenly spaced distribution within said apical frequency range than if the first band boundary determination rule was applied to the apical subset of stimulation electrodes.

The procedure further comprises a step of determining a basal frequency band for each stimulation electrode in a basal subset of stimulation electrodes based on a third band boundary determination rule, said basal frequency bands covering a basal frequency range extending between the tonotopic frequency range and said upper boundary of said frequency band associated with the most basal stimulation electrode. Herein, the "basal subset" comprises all stimulation electrodes to the basal side of said tonotopic subset of stimulation electrodes.

Similar to the case for the apical frequencies, in some embodiments, said third band boundary determination rule is likewise independent of the place frequencies of the stimulation electrodes in said basal subset.

However, as before, the invention is not limited to this, and in other embodiments it is possible that the third band boundary determination rule does account for some or all of said place frequencies associated with said basal subset. However, in this case, the third band boundary determination rule is still different from the first band boundary determination rule, and in particular leads to a distribution of boundaries that is closer to a logarithmically evenly spaced distribution within said basal frequency range than if the first band boundary determination rule was applied to the basal subset of stimulation electrodes.

The frequency mapping procedure of the invention allows for making optimum use of both, patient specific tonotopic information as well as the available hardware capabilities, and allows for processing the acoustic frequencies of interest. The inventors have noticed that if trying to define frequency bands for each of the stimulation electrodes such as to include (and possibly be centered around) the corresponding place frequency, this may lead to problems. The first problem is that the place frequency associated with the most apical electrode when inserted into the patient cochlea may be quite high, such as around 600 Hz. Lower place frequencies would require a deeper insertion, which is often not possible given the patient's anatomy. This then suggests that either the frequency band associated with the most apical electrode is extremely broad, or has a fairly high lower boundary, which however would imply that low frequencies are missed which may be important for auditory perception, and particularly for speech recognition. The second problem is that the place frequency associated with the one or more most basal electrode(s) is often higher than the frequencies supported by the preferred signal processors. In this case, the most basal stimulation electrode(s) has/have to be deactivated, thereby making inefficient use of the available hardware and reducing the number of active channels.

Normal hearing users were asked to determine the sound quality of sound samples with compressed frequency spectra. Sound samples which had their frequency spectrum compressed from 3000 Hz upwards, and an unaltered frequency spectrum below 3000 Hz were rated best meaning that subjects detected least sound quality reduction for speech signals.

It was therefore concluded that keeping the correct tonotopic matching was not equally important throughout the accessible frequency range. From experiments, the inventors concluded that the tonotopic match in an intermediate frequency range was most important for sound quality, while a tonotopic mismatch at higher frequencies was acceptable. Accordingly, the inventors concluded that it is sufficient to maintain the tonotopic matching in an intermediate frequency range, referred to as the "tonotopic frequency range" herein, and to strictly enforce the tonotopic matching only for a subset of stimulation electrodes, the "tonotopic subset", within this intermediate frequency range. The selection as to which stimulation electrodes are part of the tonotopic subset is made according to the aforementioned tonotopic subset selection criterion, and the boundaries of the respective filter bands are determined based on the aforementioned "first band boundary determination rule", which ensures a tonotopic match.

For lower frequencies, temporal fine structure (FS) stimulation has been previously utilized at the most apical electrodes. Studies found in Prentiss S, Stoecker H, Wolford B. *Ipsilateral acoustic electric pitch matching: A case study of cochlear implantation in an up-sloping hearing loss with preserved hearing across multiple frequencies. Cochlear.Implants. Int.* 2014; 15:161-165 and in Vermeire K, Punte A K, Van de Heyning P. *Better speech recognition in noise with the fine structure processing coding strategy. ORL J.Otorhinolaryngol.Relat Spec.* 2010; 72:305-311 indicate that with temporal FS stimulation, the perceived rate pitch dominates over the place pitch. Therefore, for these most apical FS channels, the place information can be neglected.

In view of this, in the procedure of the invention, a lower boundary is assigned to a frequency band associated with the most apical stimulation electrode, which is lower than 200 Hz, preferably lower than 150 Hz, and most preferably lower than 90 Hz. This lower boundary may hence be significantly lower than the place frequency of the most apical stimulation electrode, indicating a tonotopic mismatch. However, the inventors noticed that this tonotopic mismatch is acceptable since it can be compensated using temporal fine structure stimulation for the most apical stimulation electrode, and preferably for all stimulation electrodes in the "apical subset" of electrodes, i.e. the stimulation electrodes located to the apical side of the tonotopic subset. Choosing such a low lower boundary for the frequency band of the most apical stimulation electrode ensures that low frequencies in the original acoustic signal are accounted for in the stimulation, which proves to be particularly helpful for speech recognition.

Moreover, the boundaries of the frequency bands associated with the apical subset of stimulation electrodes are then distributed within the "apical frequency range" which extends between the tonotopic frequency range and the assigned lower boundary of the frequency band associated with the most apical stimulation electrode, such as to cover this apical frequency range in a suitable manner, based on the aforementioned second band boundary determination rule. As was explained above, in preferred embodiments, the second band boundary determination is generally not aimed at ensuring the tonotopic matching for the apical subset of stimulation electrodes, but rather at a favorable way of covering the apical frequency range.

Similarly, with respect to the basal end of the electrode array, the procedure comprises assigning an upper boundary to a frequency band associated with the most basal stimulation electrode. This upper boundary may be chosen according to the hardware requirement, such as the maximum frequency that can be processed by the employed signal processor. For each of the stimulation electrodes in the basal subset, frequency bands are determined based on a third band boundary determination rule, such as to cover the "basal frequency range" extending between the tonotopic frequency range and the assigned upper boundary of the frequency band associated with the most basal stimulation electrode in a suitable manner. This third band boundary determination is likewise not aimed at ensuring tonotopic matching for the basal subset of stimulation electrodes, but rather to ensure that the frequency bands of all available basal stimulation electrodes are favourably, for example "evenly" distributed within the basal frequency range, where an "even distribution" could for example be a logspace distribution or a distribution similar to it. In particular, this allows for employing all of the available stimulation electrodes, even if the place frequency associated with the most basal frequency is significantly higher than the highest frequency supported by the signal processor and the upper boundary of the corresponding frequency band is adjusted to this hardware limitation.

As indicated before, each of said stimulation electrodes may correspond to an active electrode contact of said electrode array, or a virtual electrode contact formed by cooperative operation of two or more electrode contacts.

In a preferred embodiment, at least one of said lower boundary assigned to said frequency band associated with the most apical stimulation electrode and said upper boundary of said frequency band associated with the most basal stimulation electrode is independent of the place frequency of the corresponding most apical and most basal stimulation electrode, respectively. In particular, they may correspond to a predetermined, patient-independent value, chosen for example to cover a desired total frequency range in view of hardware requirements and hearing experiments.

In a preferred embodiment, said tonotopic subset selection criterion comprises a lower and an upper frequency threshold, wherein said selection criterion is fulfilled for a stimulation electrode having a place frequency within a range between said lower and upper frequency thresholds.

Herein, said lower threshold may be between 300 Hz and 1200 Hz, preferably between 500 Hz and 1100 Hz, and most preferably between 900 Hz and 1000 Hz. The lower threshold may for example be a threshold up to which FS stimulation is feasible and allows for compensating for a tonotopic mismatch in the apical subset of stimulation electrodes.

In addition or alternatively, said upper threshold may be between 2000 Hz and 4000 Hz, preferably between 2500 Hz and 3500 Hz, and most preferably between 2700 Hz and 3300 Hz. The upper threshold is a threshold beyond which the tonotopic information becomes less important, such that the tonotopic matching can be relaxed. The threshold has been determined empirically by the inventors and is found to give a good compromise between use of tonotopic information and use of all of the available stimulation electrodes within an available frequency range in view of hardware requirements.

In preferred embodiments, said tonotopic subset selection criterion further comprises information regarding residual hearing of the patient for low frequencies, wherein in case of sufficient residual hearing, the procedure may extend said tonotopic subset all the way to the most apical stimulation electrode.

In a preferred embodiment, said procedure ensures that said tonotopic subset comprises at least two stimulation electrodes. Note that the number of stimulation electrodes within the tonotopic subset will depend on the patient-specific place frequencies and the tonotopic subset selection criterion, and it may hence vary from patient to patient. However, the procedure at any rate ensures that there will be at least two stimulation electrodes in the tonotopic subset. For example, in case the number of stimulation electrodes in said tonotopic subset turns out to be less than two, then the tonotopic subset selection criterion may be modified, or the procedure may switch to another, standard frequency matching strategy.

In a preferred embodiment, said procedure may further ensure that one or both of said apical and basal subsets comprises at least two stimulation electrodes.

In a preferred embodiment, for some or all of said stimulation electrodes, the upper boundary of the respective frequency band coincides with the lower boundary of the adjacent frequency band in basal direction. This ensures that the entire frequency range is accounted for, while avoiding unnecessary redundancies. Nevertheless, it would also be possible that the boundaries of adjacent frequency bands overlap with each other.

In a preferred embodiment, said first band boundary determination rule determines the upper and lower boundaries of said tonotopic frequency band of a given stimulation electrode based on one of an arithmetic mean, a geometrical mean or a logarithmic mean of the place frequency of the given stimulation electrode and the place frequency of a respective adjacent stimulation electrode. Alternatively, a computation rule may be used that leads to a value between said arithmetic and logarithmic mean. By relying on a "mean" between place frequencies of adjacent stimulation electrodes, be it arithmetic, geometrical or logarithmic, errors in the determined place frequencies can be compensated at least to some extent.

In a preferred embodiment, said second band boundary determination rule determines the band boundaries within said apical frequency range such that the logarithms of the boundaries are evenly spaced between the logarithm of the lower boundary of the tonotopic frequency band of the most apical stimulation electrode among the tonotopic subset and the logarithm of the lower boundary of the frequency band associated with the most apical stimulation electrode within the electrode array, or such that the logarithms of all of the boundaries deviate from the evenly spaced logarithmic values by no more than 10%, preferably no more than 8%, and most preferably no more than 6%.

In a preferred embodiment, said third band boundary determination rule determines the band boundaries within said basal frequency range such that the logarithms of the boundaries are evenly spaced between the logarithm of the upper boundary of the tonotopic frequency band of the most basal stimulation electrode among the tonotopic subset and the logarithm of the upper boundary of the frequency band associated with the most basal stimulation electrode within the electrode array, or such that the logarithms of all of the boundaries deviate from the evenly spaced logarithmic values by no more than 15%, preferably no more than 12%, and most preferably no more than 10%.

A further aspect of the invention relates to a fitting system for carrying out a patient-specific frequency mapping procedure for a cochlear implant or an electric-acoustic stimulation device having an electrode array that has been implanted into the cochlea of said patient, wherein said implanted electrode array comprises a number of stimulation electrodes at corresponding electrode locations within the cochlea, wherein said system comprises means for generating or an interface for receiving tonotopic frequency information, said tonotopic frequency information comprising, for each of said stimulation electrodes, a place frequency associated with the patient-specific location of said stimulation electrode in the cochlea where said stimulation electrode is placed, said system being further configured for determining, based on said tonotopic frequency information and a tonotopic subset selection criterion, a tonotopic subset of adjacent stimulation electrodes, for assigning a tonotopic frequency band to each stimulation electrode within said tonotopic subset based on a first band boundary determination rule, wherein said first band boundary determination rule determines an upper and a lower boundary of the tonotopic frequency band for each given stimulation electrode within said tonotopic subset, such as to ensure that the lower boundary is at a frequency that is lower than the place frequency of the given stimulation electrode but higher than the place frequency of the adjacent electrode in apical direction, and the upper boundary is at a frequency that is higher than the place frequency of the given stimulation electrode but lower than the place frequency of the adjacent electrode in basal direction, wherein said tonotopic frequency bands associated with said tonotopic subset of stimulation electrodes define a tonotopic frequency range, for assigning a lower boundary to a frequency band associated with the most apical stimulation electrode within the electrode array, said lower boundary being lower than 200 Hz, preferably lower than 150 Hz, and most preferably lower than 90 Hz, irrespectively of the place frequency of the most apical stimulation electrode, for assigning an upper boundary to a frequency band associated with the most basal stimulation electrode, said upper boundary being lower than 12.0 kHz, preferably lower than 10.0 kHz, and most preferably lower than 9.5 kHz, irrespectively of the place frequency of the most basal stimulation electrode, for determining an apical frequency band for each stimulation electrode in an apical subset of stimulation electrodes based on a second band boundary determination rule, said apical frequency bands covering an apical frequency range extending between the tonotopic frequency range and said lower boundary of said frequency band associated with the most apical stimulation electrode, wherein said apical subset comprises all stimulation electrodes to the apical side of said tonotopic subset of stimulation electrodes,

11 wherein said second band boundary determination rule is either independent of the place frequencies of the stimulation electrodes in said apical subset or, if the second band boundary determination rule does account for some or all of said place frequencies associated with said apical subset, it leads to a distribution of boundaries that is closer to a logarithmically evenly spaced distribution within said apical frequency range than if the first band boundary determination rule was applied to the apical subset of stimulation electrodes, and for determining a basal frequency band for each stimulation electrode in a basal subset of stimulation electrodes based on a third band boundary determination rule, said basal frequency bands covering a basal frequency range extending between the tonotopic frequency range and said upper boundary of said frequency band associated with the most basal stimulation electrode, wherein said basal subset comprises all stimulation electrodes to the basal side of said tonotopic subset of stimulation electrodes, wherein said third band boundary determination rule is either independent of the place frequencies of the stimulation electrodes in said basal subset or, if the second band boundary determination rule does account for some or all of said place frequencies associated with said basal subset, it leads to a distribution of boundaries that is closer to a logarithmically evenly spaced distribution within said basal frequency range than if the first band boundary determination rule was applied to the basal subset of stimulation electrodes.

In preferred embodiments, the fitting system is further configured to carry out a patient-specific frequency mapping procedure according to one of the embodiments described above. The fitting system may be a computer implemented fitting system comprising a processor for carrying out the mapping procedure and various input and/or output interfaces for receiving data, such as data representing tonotopic frequency information, or medical images from which there tonotopic frequency information can be derived by the fitting system, and for outputting information, in particular information regarding the frequency bands of the stimulation electrodes, to user or to a cochlear implant or electric-acoustic stimulation device.

A further aspect of the invention relates to a computer program product, which when the program is carried out by a computer, causes the computer to carry out a patient-specific frequency mapping procedure according to any one of the embodiments described above. The computer program product may be stored on a non-volatile data storage device.

12

FIG. 5 shows a flow diagram of a patient-specific frequency mapping procedure according to an embodiment of the invention.

FIG. 6 shows a table summarizing place frequencies associated with individual stimulation electrodes of an implanted electrode array.

Figure 1:
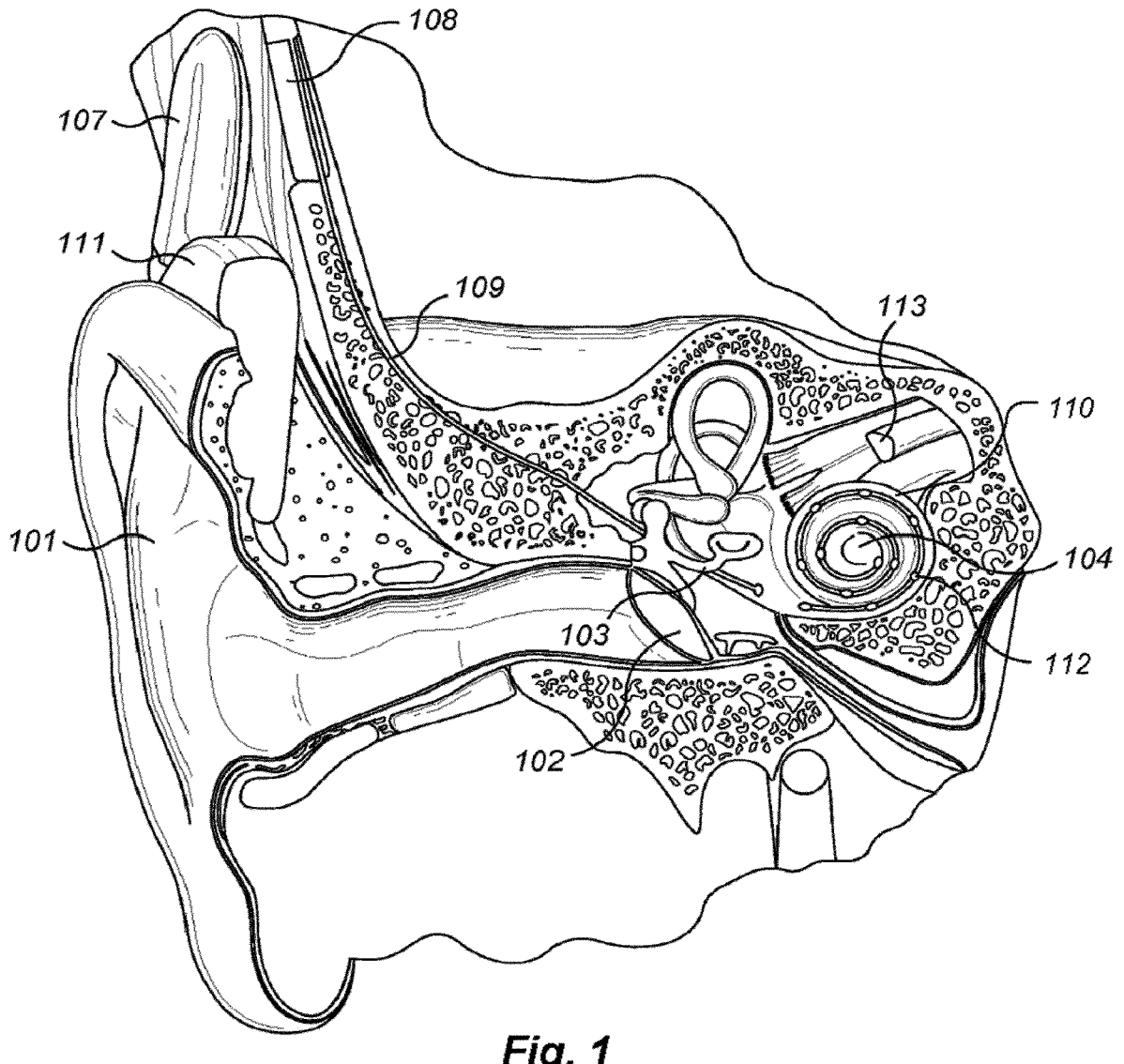
FIG. 1 shows a sectional view of a human ear with a typical cochlear implant system designed to deliver electrical stimulation to the inner ear.
Figure 2:
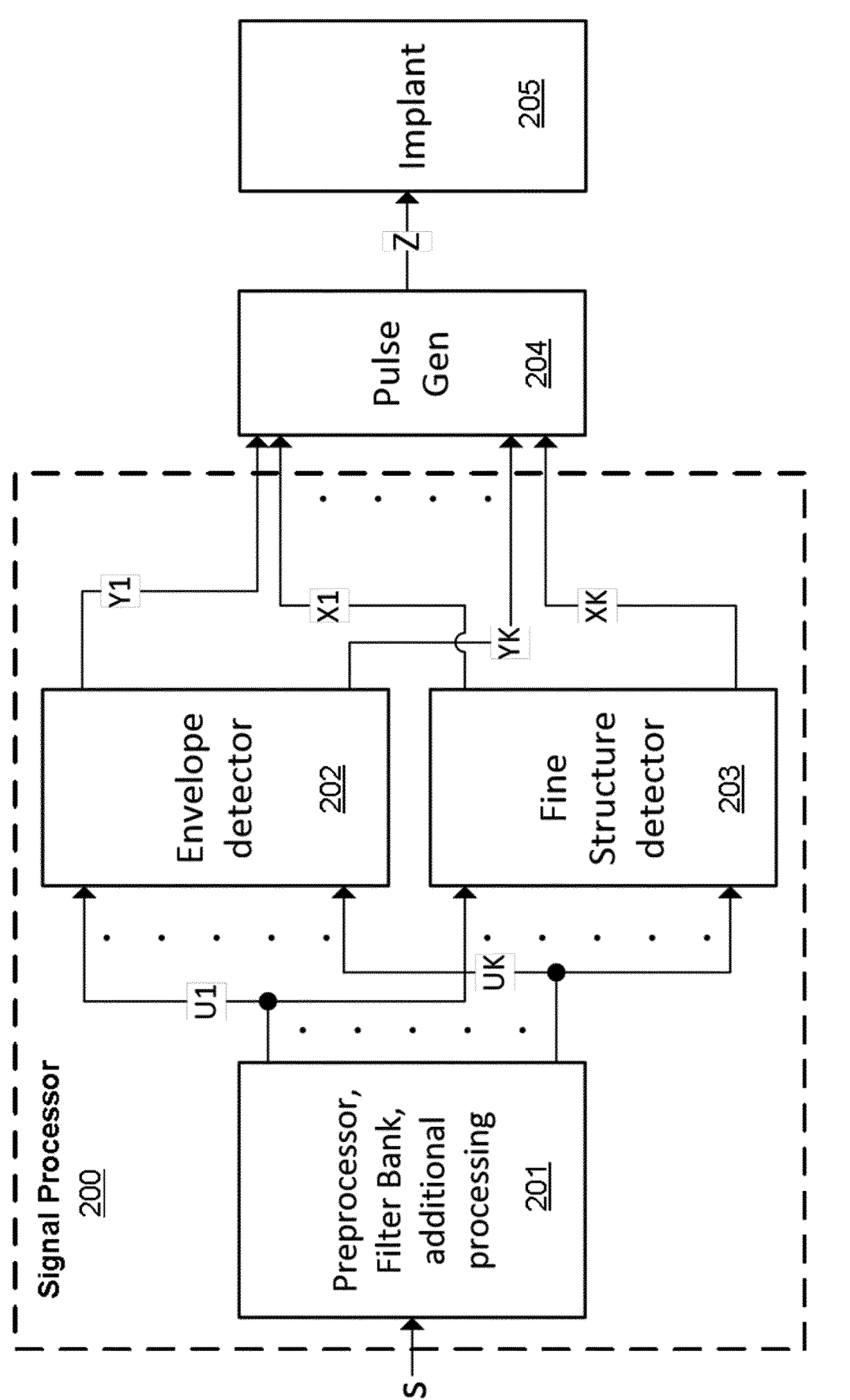
FIG. 2 shows various functional blocks in a signal processing arrangement for a hearing implant according to an embodiment of the present invention.
Figure 3:
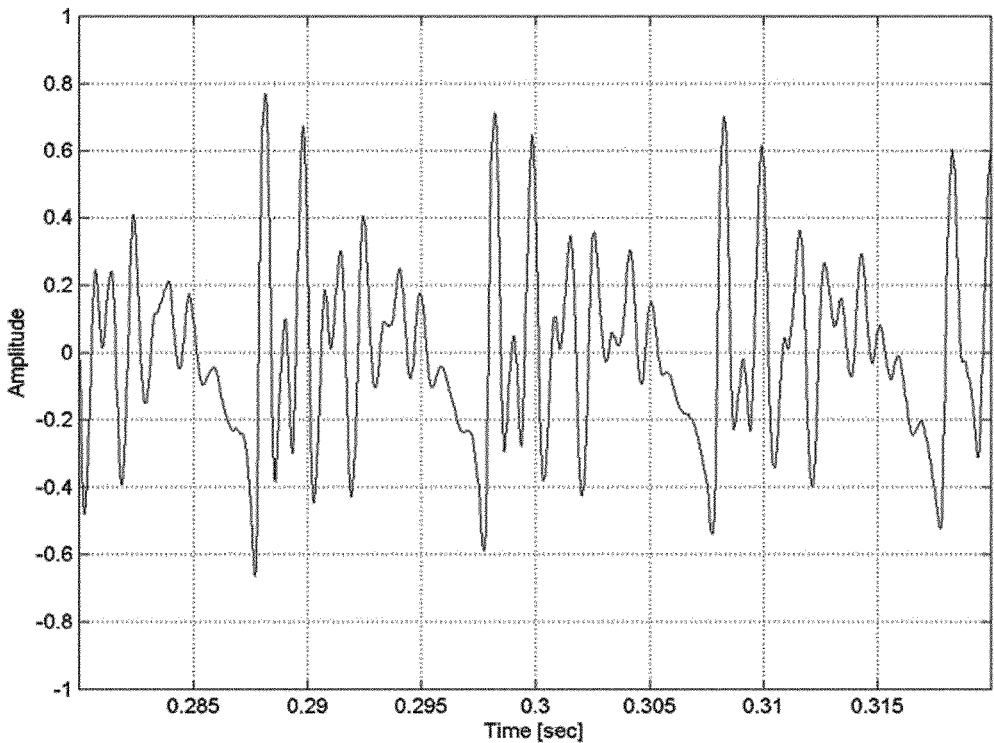
FIG. 3 shows an example of a short time period of an audio speech signal from a microphone.
Figure 4:
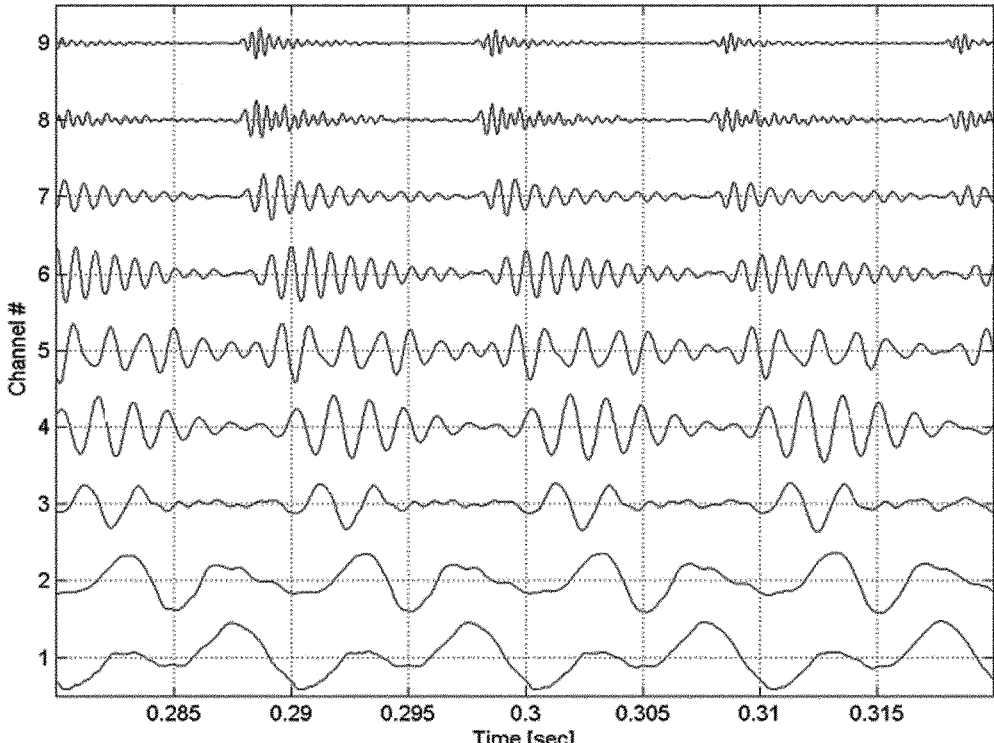
FIG. 4 shows an acoustic microphone signal decomposed by band-pass filtering by a bank of filters into a set of band pass signals.
Figures 7, 8:
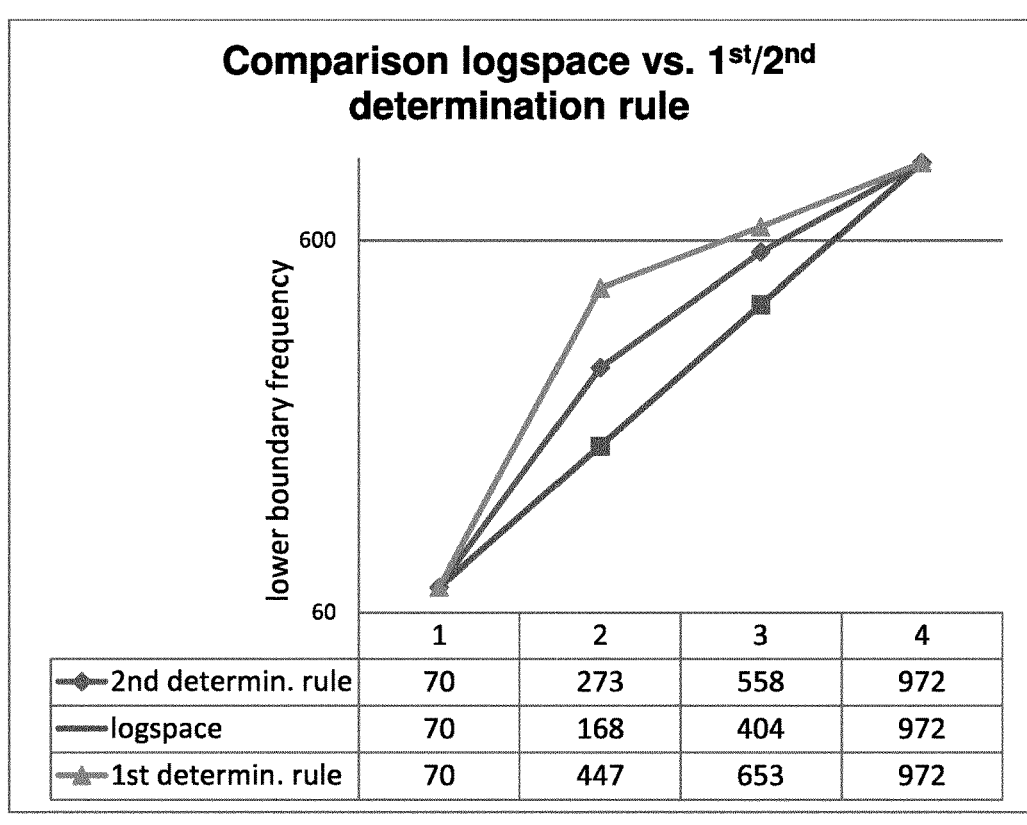

FIG. 7 shows a table exhibiting lower and upper boundaries of frequency bands associated with the stimulation electrodes of said implanted electrode array determined using a first band boundary determination rule.

FIG. 8 shows a table exhibiting lower and upper boundaries of frequency bands associated with the stimulation electrodes of said implanted electrode array determined using a first, a second and a third band boundary determination rule applied to stimulation electrodes in a tonotopic, an apical and a basal subset of stimulation electrodes, respectively.

DETAILED DESCRIPTION OF SPECIFIC EMBODIMENTS

It is to be understood that both the foregoing general description and the following description are exemplary and explanatory only and are not restrictive of the methods and devices described herein. In this application, the use of the singular may include the plural unless specifically state otherwise. Also, the use of "or" means "and/or" where applicable or unless stated otherwise. Those of ordinary skill in the art will realize that the following description is illustrative only and is not intended to be in any way limiting. Other embodiments will readily suggest themselves to such skilled persons having the benefit of this disclosure. Reference will now be made in detail to various implementations of the example embodiments as illustrated in the accompanying drawings.

With reference to FIG. 5, a patient-specific frequency mapping procedure for a cochlear implant device will be described. After a start at step 300, the procedure comprises a step of providing tonotopic frequency information. This tonotopic frequency information can be discerned from medical images, such as planar x-ray images, CT images, digital volume tomography or NMR images of an electrode array after implantation into the patient. Based on the medical image, the position of each stimulation electrode can be determined, either automatically using a suitable image processing software or manually. For example, the position of each stimulation electrode can be parameterized by an insertion angle, which represents an insertion depth of the respective stimulation electrode in the cochlea. Suitable techniques for determining the position of the stimulation electrodes are per se known from prior art, such as Cohen, L. T; Xu, J.; Xu, S. A.; Clark, G. M (1996): *Improved and simplified methods for specifying positions of the electrode bands of a cochlear implant array. In: Am J Otol* 17, S. 859-65, and Xu, J.; Xu, S. A.; Cohen, L. T; Clark, G. M (2000): *Cochlear view: postoperative radiography for cochlear implantation. In: Am J Otol* 21, S. 49-56; and therefore shall not be explained in more detail herein.

From Stakhovskaya, O.; Sridhar, D.; Bonham, B. H.; Leake, P. A. (2007): *Frequency map for the human cochlear spiral ganglion: implications for cochlear implants. In: Journal of the Association for Research in Otolaryngology: JARO* 8, S. 220-33. DOI: 10.1007/s10162-007-0076-9, the following mathematical formula is known, which defines a relationship between the distance y from the oval window and the electrode insertion angle x for two different stimulation areas of the scala tympani:

$$y(x)=Ae^{-Bx}-C$$

Herein, y(x) defines the percentage of the distance from the oval window in relation to the total area of the cochlea that is relevant for sound perception, and can hence be between 0% and 100%.

The parameters are chosen as follows:

$$y_{SG}: A = -99.3; B = 0.004; C = 105 \quad \text{for the spiral ganglion } (SG)$$

$$y_{OC}: A = -110; B = 0.002; C = 115 \quad \text{for the organ of Corti } (OC)$$

Since the implanted electrode array in the implanted state is typically between the organ of *Corti* and the spiral ganglion, for each insertion angle $x_i$, the arithmetic mean $y_m(x_i)$ of the parameter sets $y_{SG}$ and $y_{OC}$ may be calculated as follows:

$$y_m(x_i) = \frac{y_{SG}(x_i) + y_{OC}(x_i)}{2}$$

Then, using the formula known from Greenwood, D. D. (1961): *Critical Bandwidth and the Frequency Coordinates of the Basilar Membrane. In: J Acoust Soc Am* 33 (10), S. 1344-1356, a place frequency $F(x_i)$ (in Hz) associated with each position $x_i$ can be calculated:

$$F(x_i) \times D * (10^{a(1-y_m(x_i))/100} - k)$$

where the parameters can e.g., be chosen as D=165.4; a=2.1; , k=0.88. The skilled person will appreciate that this is just one exemplary way of determining the place frequencies, and that other formulae or algorithms can be used for this purpose.

In the table of FIG. 6, the place frequencies for 12 electrodes that have been determined from an implanted patient are summarized in the column titled "center frequency". As is seen therein, the place frequency determined for the most apical electrode, i.e. electrode 1, is 376 Hz, while the place frequency for the most basal stimulation electrode, electrode 12, is as high as 11874 Hz.

Next, in step 304, a tonotopic subset of adjacent stimulation electrodes is determined, based on a tonotopic subset selection criterion. In the present embodiment, the tonotopic subset selection criterion is whether the place frequency is higher than a lower threshold of 950 Hz and lower than an upper threshold of 3000 Hz. This selection criterion is fulfilled by the fourth through seventh stimulation electrodes, which are highlighted by bold font in the table of FIG. 6. Moreover, the stimulation electrodes to the apical side of the tonotopic subset are referred to herein as the apical stimulation electrodes forming an "apical subset", in this case electrodes 1 to 3. Similarly, the stimulation electrodes to the basal side of the tonotopic subset are referred to as the basal stimulation electrodes forming a "basal subset", in this case electrodes 8 to 12.

Next, in step 306, it is checked whether the number of electrodes selected as part of the tonotopic subset is 2 or more. This should usually be the case. If this should not be the case, the procedure may proceed to step 318, in which the tonotopic subset selection criterion is adjusted, for example by shifting one of the thresholds, and the procedure returns to step 304. In alternative embodiments not shown in FIG. 5, the procedure may stop if the number of electrodes in the tonotopic substrate is below 2, as this may e.g. indicate that one of the stimulation electrodes has been overlooked in the medical image, or that there was an error in the determination of the position or place frequency. In this case, the previous step 302 of providing tonotopic frequency information can be revisited, or the procedure may switch to a default frequency mapping procedure that ignores the patient-specific tonotopic information.

In step 310, a tonotopic frequency band is assigned to all stimulation electrodes in the tonotopic subset, using a corresponding first band boundary determination rule. In the embodiment shown, the first band boundary determination rule determines the upper and lower boundaries of the tonotopic frequency band of a given stimulation electrode based on a logarithmic mean of the place frequency of the given stimulation electrode and the place frequency of the respective adjacent stimulation electrode. Herein, the "logarithmic mean" of two numbers is the exponential of the arithmetic mean of the logarithms of these numbers. Moreover, this first band boundary definition further ensures that the upper and lower band boundaries of two adjacent tonotopic stimulation electrodes coincide, i.e. the individual tonotopic frequency bands cover the full tonotopic frequency range, but do not overlap, and that each place frequency lies within the corresponding frequency band.

The resulting upper and lower boundaries of each tonotopic frequency band are summarized in the table of FIG. 7. Moreover, in the table of FIG. 7, for illustration purposes only, also the upper and lower boundaries have been calculated for the apical simulation electrodes (electrodes 1 through 3) and the basal stimulation electrodes (electrodes 8 through 12). In addition, the lower boundary of the frequency band associated with the most apical electrode 1 has been set to 70 Hz, as it is believed that acoustic information down to this frequency should be accounted for in the operation of the cochlea implant. Moreover, the upper boundary of the frequency band associated with the most basal electrode 12 has been deliberately set to 8.5 kHz, as this is the maximum frequency supported by the signal processor used in the implant system. Note that the selection of the lowest and highest frequencies at 70 Hz and 8.5 kHz is in this case completely independent of the place frequencies of the stimulation electrodes, and in particular disregards the fact that e.g. the place frequency of the most basal electrode 12 at 11,874 Hz is already way beyond the frequency cut-off at 8.5 kHz.

In the table of FIG. 7, the center frequency of each frequency band has been replaced by the arithmetic mean value of its boundary frequencies, such that it does no longer coincide with the place frequency. Note that for the operation of the system, the center frequency does not have any immediate importance, since what really matters is the frequency band that is associated with each simulation electrode.

From FIG. 7, it is seen why the first band boundary determination rule when applied to all 12 stimulation electrodes is less than optimal. For example, with regard to the apical end of the electrode array, it is seen that frequency band of the most apical electrode 1 turns out to be very large, ranging from 70 to 447 Hz. Generally, the frequency bands for lower frequencies should be smaller than for higher frequencies, so that this frequency bandwidth is clearly undesirably large for such low frequencies.

Moreover, it is seen from that the place frequency of electrode 11 (8450 Hz) is already very close to the maximum supported frequency of 8500 Hz, and that the place frequency of the most basal electrode 12 (11874 Hz) is way beyond this maximum frequency. Moreover, as is seen from FIG. 7, the upper boundary of the frequency band of electrode 11 when determined according to the first band boundary determination rule would be at 10,016 Hz, and hence be beyond the upper limit of 8,500 Hz as well. Accordingly, if the first band boundary determination rule were to be used for the basal subset as well, then one would have to deactivate at least stimulation electrode 12, and presumably also stimulation electrode 11. In other words, while the first band boundary determination rule is attractive in as much as it allows for a tonotopic matching throughout the electrode array, it does not allow to make full use of the available stimulation electrodes, and it leads to unnaturally large frequency bands at the apical end.

According to the present invention, the first band boundary determination rule is hence only applied for the tonotopic subset of stimulation electrodes, while different second and third band boundary determination rules are used for the apical and basal subsets. The second and third band boundary determination rules are devised to allow for using all of the stimulation electrodes, and to lead to a more even distribution of frequency bands in the apical and basal frequency ranges, although at the price of sacrificing the tonotopically correct mapping.

The inventors have found that this still gives better overall results than a default frequency mapping, not taking account of the place frequencies at all, or a strictly tonotopic matching according to the first band boundary determination rule is applied throughout the electrode array. This is based on the observation that the tonotopic information is the most valuable for the intermediate electrodes falling under the tonotopic subset selection criterion. Namely, beyond some upper threshold value, the added benefit of the tonotopic mapping for the pitch perception is significantly less than below such a threshold value, which is why the strict tonotopic match is only enforced in the tonotopic subset of stimulation electrodes. Note that the decrease in importance of the tonotopic match with higher frequencies is gradual, and that depending on the precise formulation of the third band boundary determination rule, the tonotopic mismatch will be smaller for those basal stimulation electrodes closer to the tonotopic subset of stimulation electrodes. Accordingly, there is no single sharp upper frequency boundary to be applied in the tonotopic subset selection criterion. Instead, a certain variety of such upper boundaries have been found to work, for example upper threshold values between 500 Hz and 1100 Hz, and most preferably upper thresholds between 900 Hz and 1000 Hz.

The general purpose of the third band boundary determination rule is to determine basal frequency bands for each stimulation electrode in the basal subset such as to cover a basal frequency range extending between the tonotopic frequency range and the upper boundary of the frequency band associated with the most basal stimulation electrode 12, i.e. 8.5 kHz. Herein, the "tonotopic frequency range" ends at the upper boundary of the most basal stimulation electrode of the tonotopic subset, i.e. at the upper boundary at 3267 Hz of the frequency band of stimulation electrode 7. Since in this embodiment, adjacent frequency bands adjoin each other without overlap, what remains to be determined are the upper boundaries of the frequency bands of the stimulation electrodes 8 through 11 (or equivalently, the lower boundaries of the frequency bands of the stimulation electrodes 9 to 12).

In the embodiment shown, the third band boundary determination rule determines the band boundaries according to a logspace distribution of four boundary values between 3267 Hz and 8500 Hz. More precisely, the third band boundary determination rule determines the band boundaries within said basal frequency range such that the logarithms of the upper boundaries of the frequency bands of the electrodes 8 through 11 are evenly spaced between the logarithm of the upper boundary (3267 Hz) of the tonotopic frequency band of the most basal stimulation electrode (electrode 7) among the tonotopic subset and the logarithm of the upper boundary (8500 Hz) of the frequency band associated with the most basal stimulation electrode (electrode 12) within the electrode array. The corresponding frequency band boundaries obtained for this logspace band boundary determination rule are shown for the electrode 8 through 12 in FIG. 8.

Note that in this case, the third band boundary determination rule is per se independent of the place frequencies of the stimulation electrodes in the basal subset. The place frequency of electrode 8 does have an impact on precisely where the tonotopic frequency range ends (namely at the logarithmic mean of the place frequencies of electrodes 7 and 8), but once the boundary of the tonotopic frequency range is determined, the third band boundary determination rule determines the band boundaries for the basal subset of stimulation electrodes without accounting for their place frequencies. This also means that there will be some tonotopic mismatch. However, this mismatch will be comparatively small for basal electrodes located closer to the tonotopic subset, and only successively increase towards higher frequencies, where the benefits of tonotopic mapping are much less pronounced. For example, when looking at the frequency bands obtained for the basal stimulation electrodes 8, 9 and 10, it is seen that the corresponding place frequencies are still at least within the corresponding frequency band. Only the place frequencies of the basal stimulation electrodes 11 and 12 fall outside their frequency bands, but at these high frequencies, this tonotopic mismatch is acceptable. Moreover, the overall pitch perception is still better than if the most basal electrodes 11 and 12 were deactivated such as to maintain the tonotopic matching in view of the limited frequency supported by the signal processor.

While in the embodiment shown, the third band boundary determination rule is independent of the place frequencies of the basal subset of electrodes, the invention is not limited to this. Instead, it is conceivable to define a third band boundary determination rules that somehow do account for some or all of the place frequencies associated with the basal subset. However in this case, the third band boundary determination rule should still be such that it leads to a distribution of boundaries that is closer to a logarithmically evenly spaced distribution within said basal frequency range than if the first band boundary determination rule was applied to the basal subset of stimulation electrodes. In particular, in this case the third band boundary determination rule should preferably be such that the logarithms of all of the boundaries deviate from the evenly spaced logarithmic values by no more than 10%, preferably no more than 8%, and most preferably no more than 6%.

With respect to the apical subset, i.e. stimulation electrodes 1, 2 and 3, the apical frequency bands are determined based on a second band boundary determination rule that is different from the first band boundary determination rule. In the embodiment shown, the basal frequency range extends from the lower boundary (972 Hz) of the frequency band of the most basal stimulation electrode (electrode 4) within the tonotopic subset and the deliberately chosen lower boundary (70 Hz) of the frequency band of the most apical electrode 1. Since in the basal frequency range too, adjacent frequency bands adjoin each other without overlap, what remains to be determined are the upper boundaries of the frequency bands of the stimulation electrodes 1 and 2 (or equivalently, the lower boundaries of the frequency bands of the stimulation electrodes 2 and 3).

In this case, it would again be possible to determine the boundaries according to a logarithmically evenly spaced distribution (logspace), which would lead to band boundaries at 70 Hz, 168 Hz, 404 Hz and 972 Hz, as shown in FIG. 8. However, in the present embodiment, a different second band boundary determination rule has been employed. Under this second band boundary determination rule, first a logspace distribution between the lower boundary of the tonotopic range (i.e. 972 Hz) and a fixed value at 250 Hz is determined, leading to a preliminary distribution [250, 393, 618, 972]. In a second step, an "error" E between the desired lower boundary at 70. Hz and the fixed value at 250 Hz is determined, which in this case is E=180 Hz. If there are n electrodes in the apical subset, then the lower boundary of the frequency band of electrode 1 is corrected by subtracting E, the lower boundary of the frequency band of electrode 2 is corrected by subtracting E (n−1)/n, the lower boundary of the frequency band of electrode 3 is corrected by subtracting E (n−2)/n, and so on, such that the lower boundary of the frequency band of electrode n is corrected by subtracting subtracting E·1/n.

With reference to the specific example, the boundary frequencies are hence determined as follows: [250, 393, 618, 972]−[180, 120, 60, 0]=[70, 273, 558, 972]. The respective values are shown in the table of FIG. 8.

Using the second band boundary determination rule, the width of the frequency band associated with the most apical stimulation electrode 1 is larger than in case of the logspace distribution, but still significantly smaller than if the first band boundary determination rule was applied. The inventors found that the distribution obtained with the second band boundary determination rule actually leads to very good results. However, the deviation from the logspace distribution should not be too large, as is the case when applying the first band boundary determination rule.

In preferred embodiments, the second band boundary determination rule determines the band boundaries within said apical frequency range such that the logarithms of the boundaries are evenly spaced between the logarithm of the lower boundary (in this case 972 Hz) of the tonotopic frequency band of the most apical stimulation electrode (in this case electrode 4) among the tonotopic subset and the logarithm of the lower boundary (in this case 70 Hz) of the frequency band associated with the most apical stimulation electrode within the electrode array, or such that the logarithms of all of the boundaries deviate from the evenly spaced logarithmic values by no more than 15%, preferably no more than 12%, and most preferably no more than 10%. In the example shown, the logarithms of both of the intermediate boundaries obtained with the second band boundary determination rule deviate from the evenly spaced logarithmic values by less than 10%, whereas in case of the first band boundary determination rule, the logarithm of the lower boundary of the frequency band of electrode 2 deviates by 19% from the corresponding logspace value.

As before, the second band boundary determination rule determines the boundaries in the apical frequency range independently of the place frequencies of the stimulation electrodes of the apical subset. Similar to the situation described for the basal frequency range above, the boundary of the tonotopic frequency range depends on the place frequency of the adjacent apical stimulation electrode (electrode 3), but when it comes to distributing the intermediate boundaries within the apical frequency range, which starts at the thus determined lower boundary of the tonotopic frequency range, the individual place frequencies of the stimulation electrodes of the apical subset are not taken into consideration.

Again, it may be possible to define a different second band boundary determination rule which does somehow take the place frequency of some or all of the stimulation electrodes within the apical subset in consideration. However, in this case, it should nevertheless lead to a distribution of boundaries that is closer to a logarithmically evenly spaced distribution within said apical frequency range than if the first band boundary determination rule was applied to the apical subset of stimulation electrodes.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions may embody all or part of the functionality previously described herein with respect to the system. Those skilled in the art should appreciate that such computer instructions can be written in a number of programming languages for use with many computer architectures or operating systems.

Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A patient-specific frequency mapping procedure for a cochlear implant or an electricacoustic stimulation device, the cochlear implant or the electroacoustic stimulation device having an electrode array that has been implanted into the cochlea of said patient, wherein said implanted electrode array comprises a number of stimulation electrodes at corresponding electrode locations within the cochlea, wherein said procedure comprises:

providing or receiving tonotopic frequency information, said tonotopic frequency information comprising, for each of said stimulation electrodes, a place frequency associated with the patient-specific location of said stimulation electrode in the cochlea where said stimulation electrode is placed, determining, using said tonotopic frequency information and a tonotopic subset selection criterion, a tonotopic subset of adjacent stimulation electrode(s), assigning a tonotopic frequency band to each stimulation electrode within said tonotopic subset using a first band boundary determination rule, wherein said first band boundary determination rule determines an upper and a lower boundary of the tonotopic frequency band for each given stimulation electrode within said tonotopic subset, such as to ensure that the lower boundary is at a frequency that is lower than the place frequency of the given stimulation electrode but higher than the place frequency of the adjacent electrode in apical direction, and the upper boundary is at a frequency that is higher than the place frequency of the given stimulation electrode but lower than the place frequency of the adjacent electrode in basal direction, wherein said tonotopic frequency band(s) associated with said tonotopic subset of stimulation electrode(s) define a tonotopic frequency range, assigning a lower boundary to a frequency band associated with the most apical stimulation electrode within the electrode array, said lower boundary being lower than 200 Hz irrespectively of the place frequency of the most apical stimulation electrode, assigning an upper boundary to a frequency band associated with the most basal stimulation electrode, said upper boundary being lower than 20 kHz, irrespectively of the place frequency of the most basal stimulation electrode, determining an apical frequency band for each stimulation electrode in an apical subset of stimulation electrode(s) using a second band boundary determination rule, said apical frequency band(s) covering an apical frequency range extending between the tonotopic frequency range and said lower boundary of said frequency band associated with the most apical stimulation electrode, wherein said apical subset comprises all stimulation electrode(s) to the apical side of said tonotopic subset of stimulation electrode(s), wherein said second band boundary determination rule is either independent of the place frequencies of the stimulation electrode(s) in said apical subset or, when the second band boundary determination rule does account for some or all of said place frequencie(s) associated with said apical subset, a distribution of boundaries is provided that is closer to a logarithmically evenly spaced distribution within said apical frequency range than if the first band boundary determination rule was applied to the apical subset of stimulation electrode(s), and determining a basal frequency band for each stimulation electrode in a basal subset of stimulation electrode(s) using a third band boundary determination rule, said basal frequency band(s) covering a basal frequency range extending between the tonotopic frequency range and said upper boundary of said frequency band associated with the most basal stimulation electrode, wherein said basal subset comprises all stimulation electrode(s) to the basal side of said tonotopic subset of stimulation electrode(s), wherein said third band boundary determination rule is either independent of the place frequencies of the stimulation electrodes in said basal subset or, when the second band boundary determination rule does account for some or all of said place frequencie(s) associated with said basal subset, a distribution of boundaries is provided that is closer to a logarithmically evenly spaced distribution within said basal frequency range than if the first band boundary determination rule was applied to the basal subset of stimulation electrode(s) and;

delivering electrical stimulation from the electrode array using the determined tonotopic subset, apical frequency band, and basal frequency band, and the assigned boundaries.

2. The procedure of claim 1, wherein each of said stimulation electrodes corresponds to an active electrode contact of said electrode array, or wherein said procedure includes forming a virtual electrode contact by cooperative operation of two or more electrode contacts.

3. The procedure of claim 1, wherein at least one of said lower boundary assigned to said frequency band associated with the most apical stimulation electrode and said upper boundary of said frequency band associated with the most basal stimulation electrode is independent of the place frequency of the corresponding most apical and most basal stimulation electrode, respectively, and is a predetermined, patient-independent value.

4. The procedure of claim 1, wherein said tonotopic subset selection criterion comprises a lower and an upper frequency threshold, wherein said selection criterion is fulfilled for a stimulation electrode having a place frequency within a range between said lower and upper frequency thresholds.

5. The procedure of claim 4, wherein said lower threshold is between 900 Hz and 1000 Hz.

6. The procedure of claim 4, wherein said upper threshold is between 2700 Hz and 3300 Hz.

7. The procedure of claim 4, wherein said tonotopic subset selection criterion further comprises information regarding residual hearing of the patient for low frequencies, wherein in case of sufficient residual hearing, the procedure extends said tonotopic subset all the way to the most apical stimulation electrode.

8. The procedure of claim 1, wherein said procedure ensures that said tonotopic subset comprises at least two stimulation electrodes.

9. The procedure of claim 1, wherein said procedure ensures that one or both of said apical and basal subsets comprises at least two stimulation electrodes.

10. The procedure of claim 1, wherein for some or all of said stimulation electrodes, the upper boundary of the respective frequency band coincides with the lower boundary of the adjacent frequency band in basal direction.

11. The procedure of claim 1, wherein said first band boundary determination rule determines the upper and lower boundaries of said tonotopic frequency band of a given stimulation electrode using one of an arithmetic mean, a geometrical mean or a logarithmic mean of the place frequency of the given stimulation electrode and the place frequency of a respective adjacent stimulation electrode, or using a computation rule that leads to a value between said arithmetic and logarithmic mean.

12. The procedure of claim 1, wherein said second band boundary determination rule determines the band boundaries within said apical frequency range such that the logarithms of the boundaries are evenly spaced between the logarithm of the lower boundary of the tonotopic frequency band of the most apical stimulation electrode among the tonotopic subset and the logarithm of the lower boundary of the frequency band associated with the most apical stimulation electrode within the electrode array, or such that the logarithms of all of the boundaries deviate from the evenly spaced logarithmic values by no more than 10%.

13. The procedure of claim 1, wherein said third band boundary determination rule determines the band boundaries within said basal frequency range such that the logarithms of the boundaries are evenly spaced between the logarithm of the upper boundary of the tonotopic frequency band of the most basal stimulation electrode among the tonotopic subset and the logarithm of the upper boundary of the frequency band associated with the most basal stimulation electrode within the electrode array, or such that the logarithms of all of the boundaries deviate from the evenly spaced logarithmic values by no more than 15%.

14. A non-transitory computer readable medium having instructions that when executed by a computer, perform the method of claim 1.

15. A fitting system for carrying out a patient-specific frequency mapping procedure for a cochlear implant or an electric-acoustic stimulation device, the cochlear implant or the electric-acoustic stimulation device having an electrode array that has been implanted into the cochlea of said patient, wherein said implanted electrode array comprises a number of stimulation electrodes at corresponding electrode locations within the cochlea, said system comprising:

means for generating or an interface for receiving tonotopic frequency information, said tonotopic frequency information comprising, for each of said stimulation electrodes, a place frequency associated with the patient-specific location of said stimulation electrode in the cochlea where said stimulation electrode is placed, a signal processor configured to:

determine, using said tonotopic frequency information and a tonotopic subset selection criterion, a tonotopic subset of adjacent stimulation electrode(s), for assigning a tonotopic frequency band to each stimulation electrode within said tonotopic subset using a first band boundary determination rule, wherein said first band boundary determination rule determines an upper and a lower boundary of the tonotopic frequency band for each given stimulation electrode within said tonotopic subset such as to ensure that the lower boundary is at a frequency that is lower than the place frequency of the given stimulation electrode but higher than the place frequency of the adjacent electrode in apical direction, and the upper boundary is at a frequency that is higher than the place frequency of the given stimulation electrode but lower than the place frequency of the adjacent electrode in basal direction, wherein said tonotopic frequency band(s) associated with said tonotopic subset of stimulation electrode(s) define a tonotopic frequency range, for assigning a lower boundary to a frequency band associated with the most apical stimulation electrode within the electrode array, said lower boundary being lower than 200 Hz, irrespectively of the place frequency of the most apical stimulation electrode, the signal processor further configured to:

assigning an upper boundary to a frequency band associated with the most basal stimulation electrode, said upper boundary being lower than 20 kHz, irrespectively of the place frequency of the most basal stimulation electrode, and determining an apical frequency band for each stimulation electrode in an apical subset of stimulation electrode(s) using a second band boundary determination rule, said apical frequency band(s) covering an apical frequency range extending between the tonotopic frequency range and said lower boundary of said frequency band associated with the most apical stimulation electrode, wherein said apical subset comprises all stimulation electrodes to the apical side of said tonotopic subset of stimulation electrode(s), wherein said second band boundary determination rule is either independent of the place frequencie(s) of the stimulation electrode(s) in said apical subset or, when the second band boundary determination rule does account for some or all of said place frequencie(s) associated with said apical subset, a distribution of boundaries is provided that is closer to a logarithmically evenly spaced distribution within said apical frequency range than if the first band boundary determination rule was applied to the apical subset of stimulation electrode(s), and the signal processor further configured to:

determine a basal frequency band for each stimulation electrode in a basal subset of stimulation electrode(s) using a third band boundary determination rule, said basal frequency band(s) covering a basal frequency range extending between the tonotopic frequency range and said upper boundary of said frequency band associated with the most basal stimulation electrode, wherein said basal subset comprises all stimulation electrode(s) to the basal side of said tonotopic subset of stimulation electrode(s), wherein said third band boundary determination rule is either independent of the place frequencie(s) of the stimulation electrode(s) in said basal subset or, when the second band boundary determination rule does account for some or all of said place frequencie(s) associated with said basal subset, a distribution of boundaries is provided that is closer to a logarithmically evenly spaced distribution within said basal frequency range than if the first band boundary determination rule was applied to the basal subset of stimulation electrode(s) and;

a pulse generator configured to deliver electrical stimulation from the electrode array using the determined tonotopic subset, apical frequency band, and basal frequency band, and the assigned boundaries.

\* \* \* \* \*